US012808767B2

(12) United States Patent
Ferry et al.

(10) Patent No.: US 12,808,767 B2
(45) Date of Patent: Nov. 24, 2026

(54) DEVICE FOR MEASURING FLUID VISCOSITY HAVING HYDROPHILIC AND HYDROPHOBIC SURFACES

(71) Applicant: Medtronic, Inc., Minneapolis, MN (US)

(72) Inventors: Brian Joseph Ferry, Saint Louis Park, MN (US); Samuel A. Bartholomew, Brooklyn Park, MN (US); Shana Lahaye Sommerfeldt, Crystal, MN (US); Michael L. Laxen, Minneapolis, MN (US); Nicholas Hofmann, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 363 days.

(21) Appl. No.: 18/425,163

(22) Filed: Jan. 29, 2024

(65) Prior Publication Data

US 2024/0255405 A1 Aug. 1, 2024

Related U.S. Application Data

(60) Provisional application No. 63/482,168, filed on Jan. 30, 2023.

(51) Int. Cl.

| | |
|---|---|
| ***G01N 11/12*** | (2006.01) |
| ***G01N 11/14*** | (2006.01) |
| ***G01N 11/16*** | (2006.01) |
| ***G01N 33/49*** | (2006.01) |

(52) U.S. Cl.

CPC ............. *G01N 11/12* (2013.01); *G01N 11/14* (2013.01); *G01N 11/16* (2013.01); *G01N 33/49* (2013.01); *G01N 2011/147* (2013.01)

(58) Field of Classification Search

CPC ........ G01N 11/10; G01N 11/12; G01N 11/14; G01N 2011/147; G01N 11/16; G01N 11/162; G01N 11/165; G01N 33/49; G01N 33/4905

See application file for complete search history.

(56) References Cited

U.S. PATENT DOCUMENTS 5,629,209 A 5/1997 Braun, Sr. et al.
6,613,286 B2 9/2003 Braun, Sr. et al.
2007/0014695 A1 * 1/2007 Yue .................. B01L 3/502707 422/400

(Continued)

OTHER PUBLICATIONS

Romano et al., "Mechanical durability of hydrophobic surfaces fabricated by injection moulding of laser-induced textures", Applied Surface Science, vol. 476, 2019, pp. 850-860.

*Primary Examiner* — Paul M. West
(74) *Attorney, Agent, or Firm* — Michael Best & Friedrich LLP

(57) ABSTRACT

A device is provided for measuring the viscosity of a fluid. The device includes a cartridge having an injection port configured to introduce fluid into the cartridge, a plurality of inlet conduits coupled to and extending away from the injection port, and a plurality of wells. The inlet conduits extend from the injection port to the wells, and are configured to deliver the fluid from the injection port to the wells. The cartridge also includes a plurality of ferromagnetic elements configured to sit within the wells. Each of the ferromagnetic elements includes a hydrophilic coating.

15 Claims, 12 Drawing Sheets

(56) References Cited

U.S. PATENT DOCUMENTS

| | | | |
|---|---|---|---|
| 2008/0160601 | A1 | 7/2008 | Handique |
| 2008/0182301 | A1 | 7/2008 | Handique et al. |
| 2021/0123903 | A1 * | 4/2021 | Meng ............... G01N 33/54366 |
| 2023/0142816 | A1 * | 5/2023 | Vasilakis ............. B01L 3/50273 435/7.92 |
| 2024/0253048 | A1 | 8/2024 | Ferry et al. |

* cited by examiner

| Cartridge Type | % Wells W/Bubbles | % Wells W/Bubbles Ø1mm Or Larger | N (Wells) |
|---|---|---|---|
| Siloxane (Round) | 0.00% | 0.00% | 66 |
| Without Siloxane (Round) | 30.00% | 30.00% | 30 |
| Mod17 (Elliptical) | 5.56% | 2.78% | 72 |

DEVICE FOR MEASURING FLUID VISCOSITY HAVING HYDROPHILIC AND HYDROPHOBIC SURFACES

CROSS-REFERENCE TO RELATED APPLICATIONS

This application claims priority to U.S. Application No. 63/482,168, filed Jan. 30, 2023, the entire contents of which are incorporated herein by reference.

FIELD

The present technology is generally related to devices for measuring the viscosity of a fluid, such as blood.

BACKGROUND

Hemostasis management plays an important role in the health and well-being of the circulatory system. Current devices for hemostasis management measure blood factors, some by changes in viscosity while agitating a blood sample, so that appropriate dosages of heparin, protamine, or other substances may be prescribed to bring the blood to desired levels of coagulation. Such devices commonly include the use of a cartridge having wells that receive the blood sample. The cartridges further include ferromagnetic elements that are moved through the blood within the wells. The devices measure the time required to move the ferromagnetic elements through the blood, and thereby determine a viscosity of the blood sample. Examples of such devices are described, for example, in U.S. Pat. Nos. 5,629,209 and 6,613,286, the entire contents of which are incorporated herein by reference.

SUMMARY

The techniques of this disclosure generally relate to the use of hydrophilic and hydrophobic surfaces on a device for measuring the viscosity of a fluid (e.g., blood), to control movement of air within the device.

In one aspect, the present disclosure provides a device for measuring the viscosity of a fluid. The device includes a cartridge main body having an injection port configured to introduce fluid into the cartridge, a plurality of inlet conduits coupled to and extending away from the injection port, and a plurality of wells. The inlet conduits extend from the injection port to the wells, and are configured to deliver the fluid from the injection port to the wells. The device also includes a plurality of ferromagnetic elements configured to sit within the wells, and the cartridge main body includes a hydrophilic surface to inhibit the formation of air bubbles within the wells.

In another aspect, the present disclosure provides a device for measuring the viscosity of a fluid. The device includes a cartridge having an injection port configured to introduce fluid into the cartridge, a plurality of inlet conduits coupled to and extending away from the injection port, and a plurality of wells. The inlet conduits extend from the injection port to the wells, and are configured to deliver the fluid from the injection port to the wells. The cartridge also includes a plurality of outlet conduits, and a plurality of vents. The outlet conduits extend from the wells to the vents, and each of the outlet conduits includes a hydrophobic surface.

In another aspect, the present disclosure provides a method of manufacturing a device for measuring the viscosity of a fluid. The method includes providing a cartridge. The cartridge has an injection port configured to introduce fluid into the cartridge, a plurality of inlet conduits coupled to and extending away from the injection port, and a plurality of wells. The inlet conduits extend from the injection port to the wells, and are configured to deliver the fluid from the injection port to the wells. The cartridge also includes a plurality of outlet conduits, and a plurality of vents. The outlet conduits extend from the wells to the vents. The method includes applying a hydrophilic coating to each of a plurality ferromagnetic elements, inserting the ferromagnetic elements into the wells, and forming a hydrophobic surface on each of the outlet conduits.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
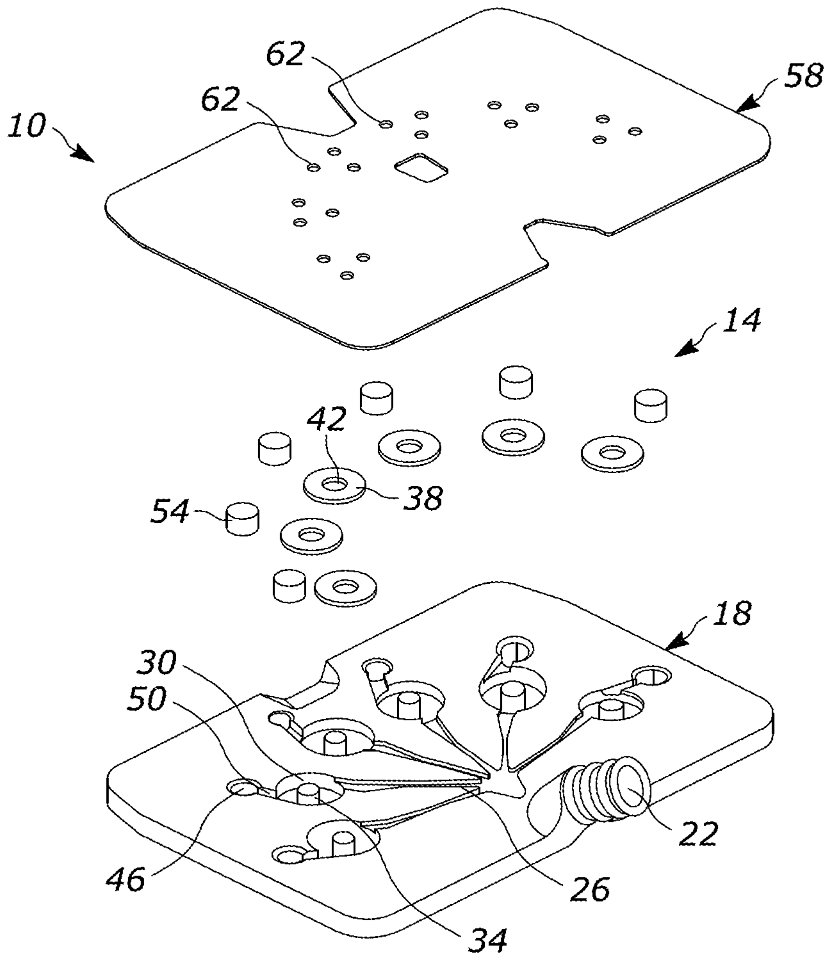
FIG. 1 is a perspective, exploded view of a cartridge for a device that measures fluid viscosity, according to one example.
Figure 2:
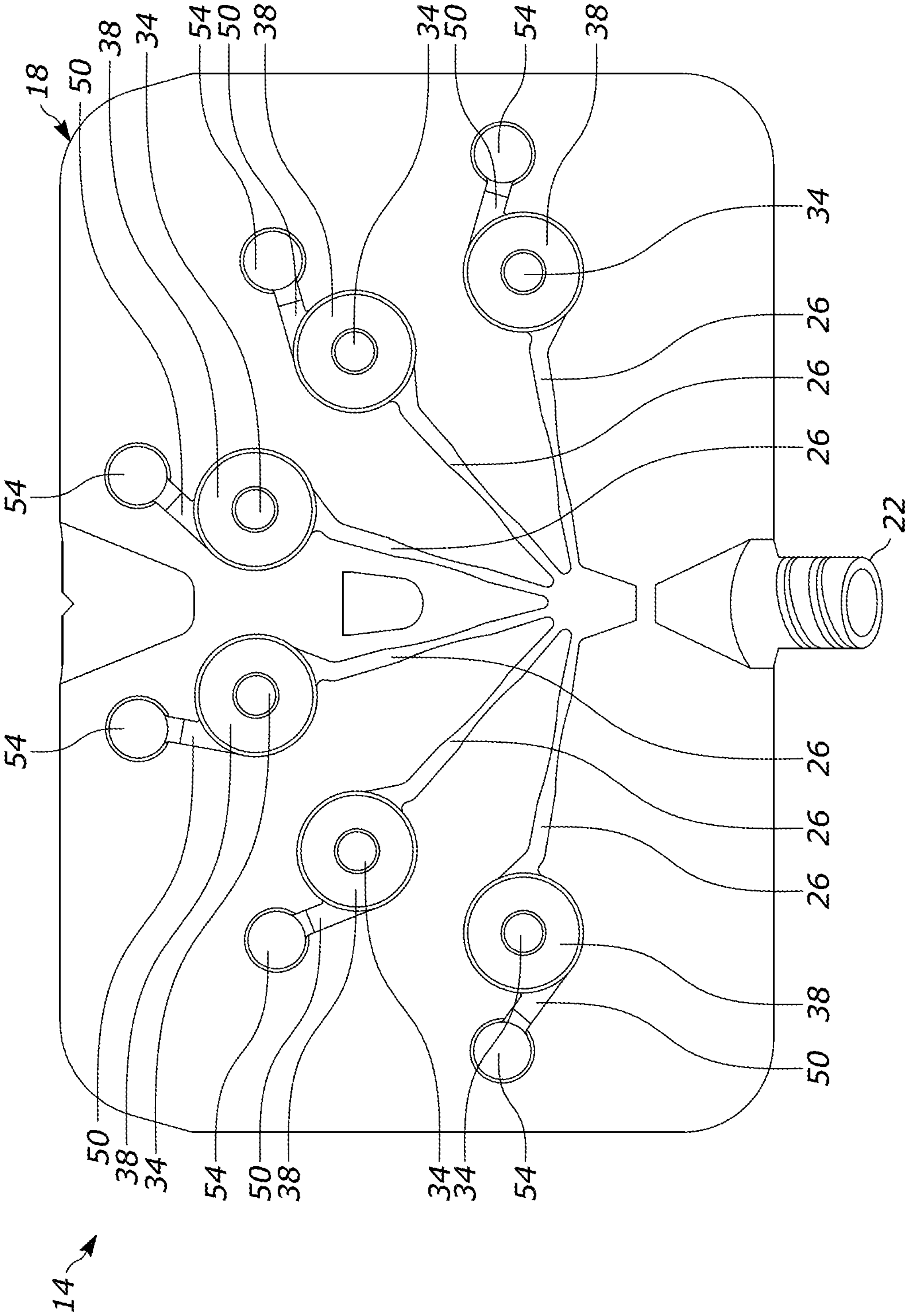
FIG. 2 is a top plan view of the cartridge.
Figure 3:
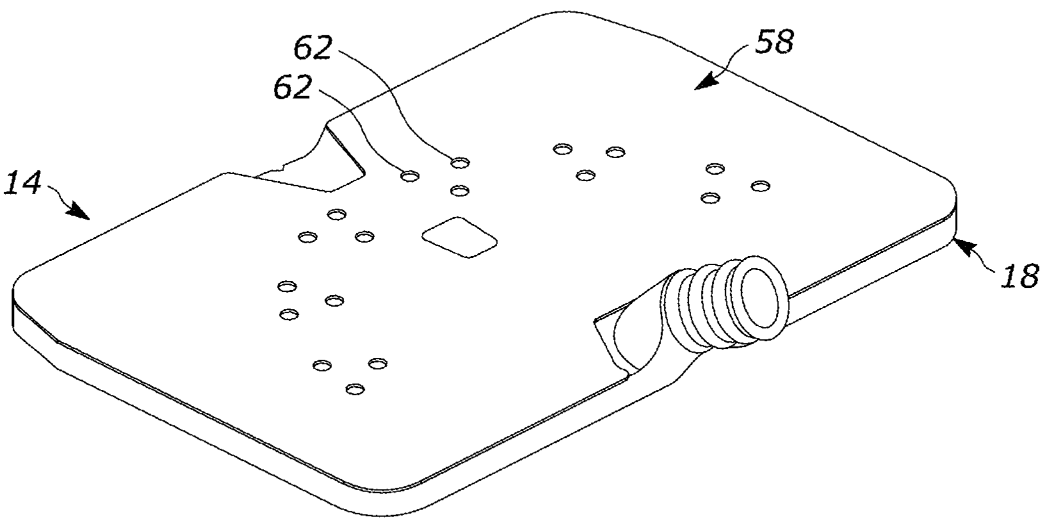
FIG. 3 is a perspective view of the cartridge.

With reference to FIGS. 1-3, a device 10 is used to measure the viscosity of a fluid (e.g., blood, industrial fluid, oil, food product liquid, etc.). The device 10 includes a cartridge 14 (e.g., disposable cartridge) having a main body 18, and an injection port 22 coupled to the main body 18 (e.g., integrally formed as a single piece with the main body 18). The injection port 22 is used to introduce fluid into the cartridge 14. The main body 18 of the cartridge 14 includes a plurality of inlet conduits 26 that extend away from the injection port 22, and a plurality of wells 30. In some examples, the main body 18 is formed of a plastic or acrylic, although other examples may include other materials.

In the illustrated example, each of the wells 30 is generally circular in shape, and includes a center post 34, although in other examples the wells 30 are oval-shaped, or have other shapes than that illustrated. The inlet conduits 26 extend from the injection port 22 to the wells 30, and deliver fluid from the injection port 22 to the wells 30 (e.g., simultaneously). Other examples include different numbers and arrangements of inlet conduits 26 and wells 30 than that illustrated. For example, in some examples the cartridge 14 includes fewer than six wells 30 (e.g., two wells 30, or three wells 30), and in other examples the cartridge 14 includes more than six wells 30 (e.g., eight wells 30, or ten wells 30).

With continued reference to FIGS. 1-3, the cartridge 14 also includes a plurality of ferromagnetic elements 38 that are sized and shaped to fit within the wells 30 of the main body 18. In the illustrated example, each of the ferromagnetic elements 38 is a washer-like element, having a circular shape and a central aperture 42. The ferromagnetic elements 38 are sized and shaped such that the central apertures 42 fit over the center posts 34, and such that the ferromagnetic elements 38 are movable within the wells 30 (e.g., vertically up and down). During operation of the device 10 (e.g., when the cartridge 14 has been inserted), each of the ferromagnetic elements 38 may be raised under a magnetic action within the well 30, and then allowed to fall through the liquid (e.g., blood) within the well 30. One or more characteristics (e.g., the time it takes for the ferromagnetic element 38 to fall through the liquid) may be measured by detecting the position of the ferromagnetic element 38. The ferromagnetic elements 38 may be raised and lowered repeatedly, and the timing may be measured, to detect a viscosity level of the fluid within the well 30, and to detect a change in viscosity (e.g., coagulation) over time. Other examples include other numbers and shapes of ferromagnetic elements 38 than that illustrated (e.g., oval-shaped ferromagnetic elements 38).

With continued reference to FIGS. 1-3, the main body 18 of cartridge 14 also includes a plurality of air vent apertures 46, and a plurality of outlet conduits 50 that extend from the wells 30 to the air vent apertures 46. The cartridge 14 includes a plurality of air vent/fluid plug devices 54 that are positioned (e.g., pressed) at least partially within the air vent apertures 46. Each of the air vent/fluid plug devices 54 inhibits, or prevents, fluid from passing further through the air vent aperture 46, but allows air to pass therethrough and into (e.g., through) the air vent aperture 46. In some examples, the air vent/fluid plug device 54 forms a permanent liquid lock. In some examples, the air vent/fluid plug device 54 is formed from plastic (e.g., Porex® plastic), although other examples include other types of material.

With continued reference to FIGS. 1-3, the cartridge 14 also includes a cover 58 that is coupled (e.g., via heat sealing) to the main body 18 of the cartridge 14. In some examples, the cover 58 is more flexible than the main body 18, is thinner than the main body 18, and/or is formed of a different material than the main body 18. In the illustrated example, the cover 58 includes a plurality of dimples 62. The dimples 62 are positioned above the wells 30, and project inwardly (i.e., toward the wells 30) when the cover 58 is coupled to the main body 18. The dimples 62 provide points of contact for the ferromagnetic elements 38, such that when the ferromagnetic elements 38 rise up within the wells 30 under magnetic force, the ferromagnetic elements 38 engage only the surface of the dimples 62, rather than engaging an entire planar region of the cover 58. This may advantageously inhibit or prevent the ferromagnetic elements 38 from sticking to the cover 58. Other examples include different number or arrangements of dimples 62, or include no dimples 62.

Figure 4:
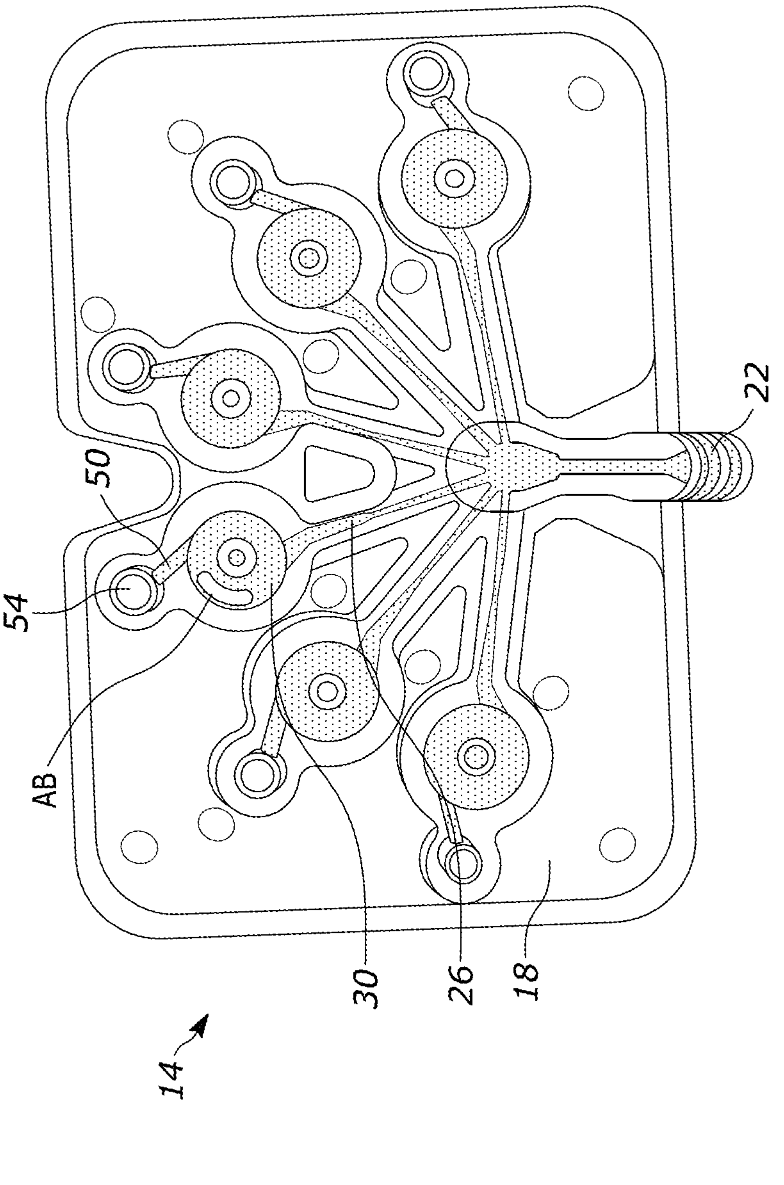
FIG. 4 is a top plan view of the cartridge, illustrating a blood sample disposed within wells in the cartridge, and a large air bubble within one of the wells.

With reference to FIG. 4, one challenge of filling the cartridge 14 (e.g., a sealed, plastic cartridge 14) with a blood sample is reducing or eliminating the formation of air bubbles within the wells 30, such as the air bubble “AB” illustrated in FIG. 4. Air bubbles in the wells 30 will affect reagent concentration with blood, and also prohibit proper lift and drop of the ferromagnetic elements 38 within the wells 30.

Figure 5:
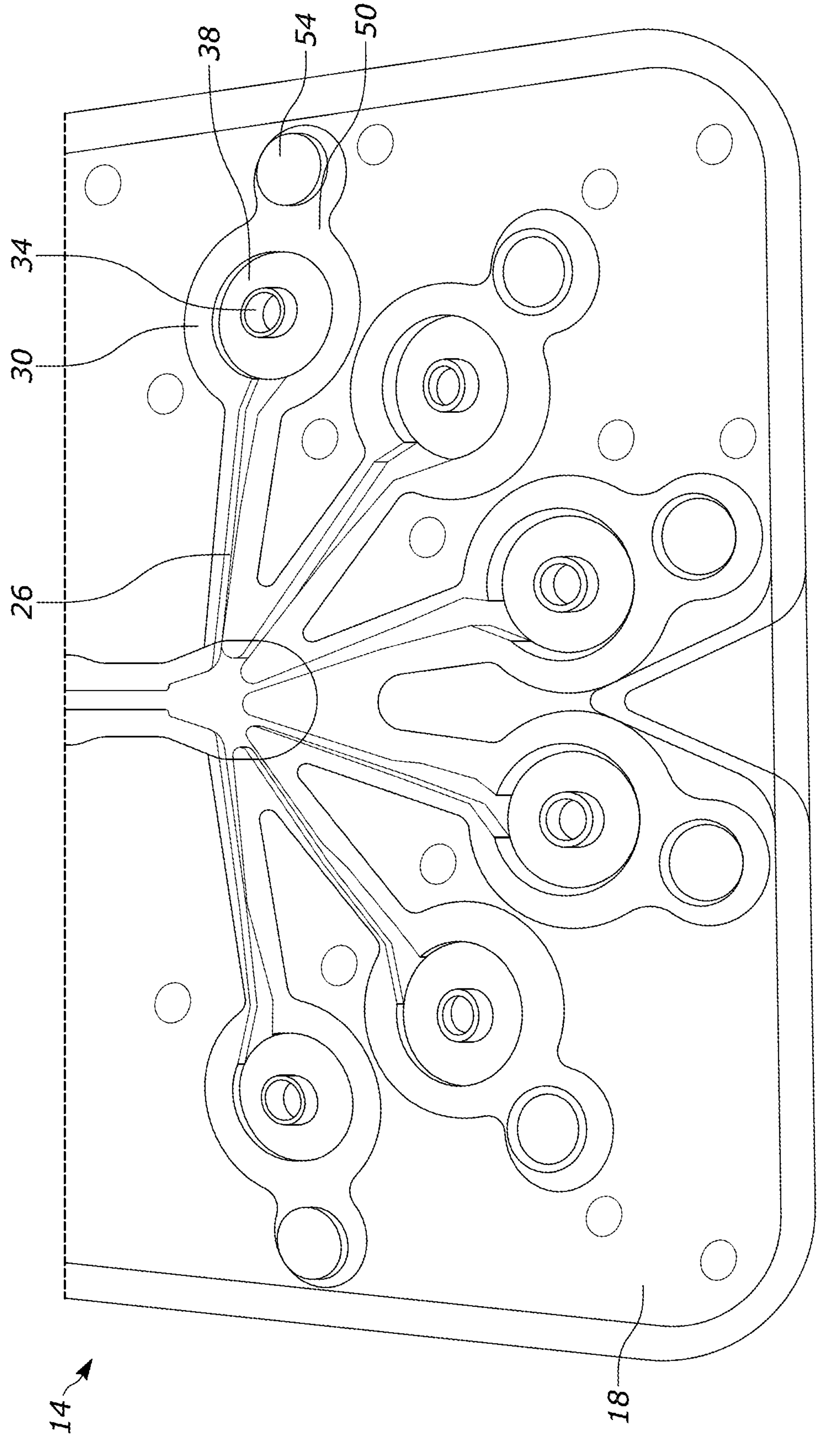
FIG. 5 is a top plan view of a cartridge according to another example, having ferromagnetic elements that are coated in hydrophilic material, and a cartridge body that is plasma-treated.
Figure 6:
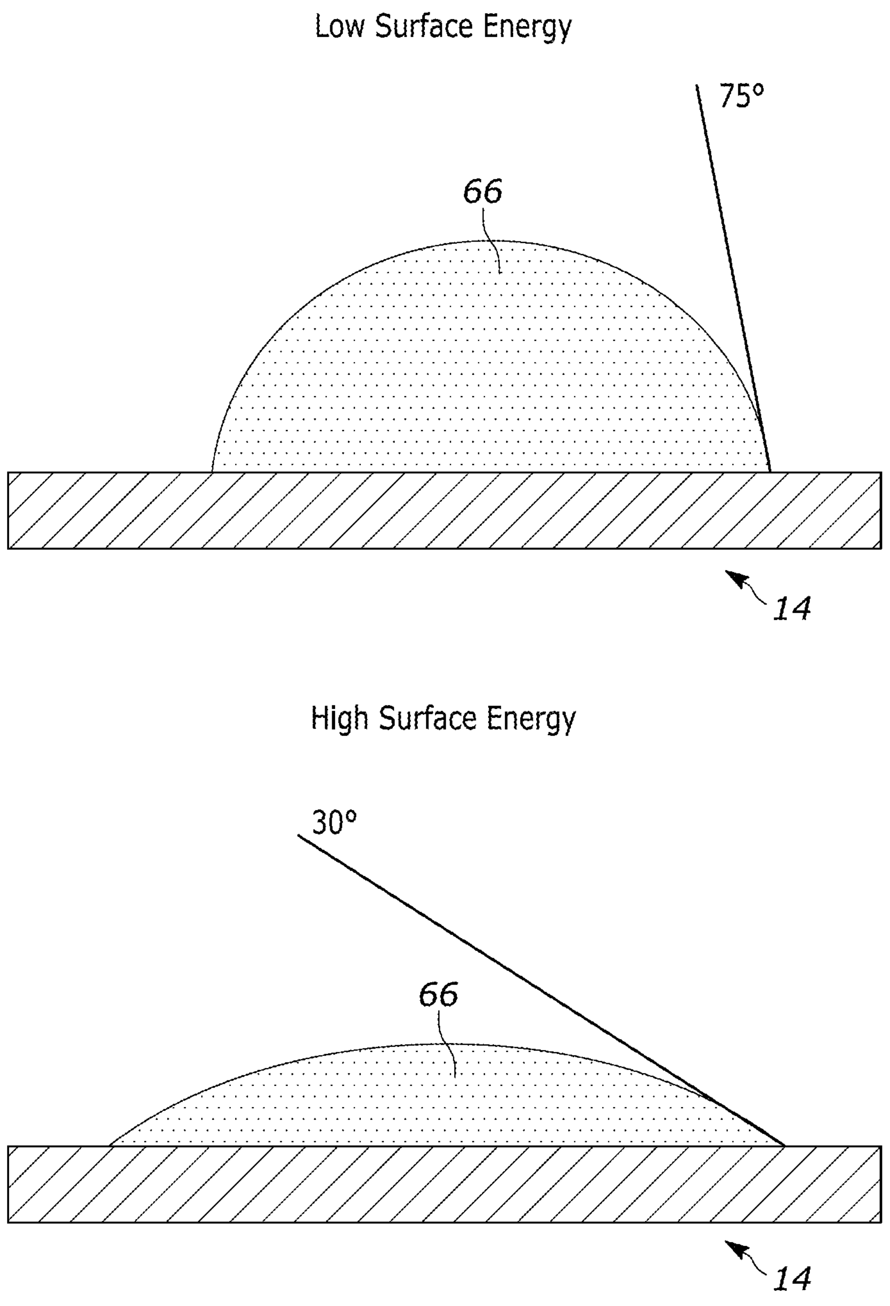
FIG. 6 is a schematic illustration of surface energy, demonstrating how the treated cartridge body may lower a contact angle.

Therefore, and with reference to FIGS. 5 and 6, in some examples at least a portion of the cartridge 14 (e.g., a surface of the cartridge 14 that defines the wells 30) is plasma treated prior to use, to form a hydrophilic surface that inhibits the formation of air bubbles. Plasma treating the cartridge 14 has been found to greatly lower a contact angle, and thus increase the surface energy along the surface of the cartridge 14. As illustrated in FIG. 6, the contact angle refers, for example, to an angle between the surface of the cartridge 14 and a tangent line to a droplet 66 of liquid (e.g., blood or water) that sits on the surface. As illustrated in FIG. 6, in some examples the plasma treatment may reduce the contact angle from 75 degrees (signifying a low surface energy for the cartridge 14) to an angle of 30 degrees (signifying a high surface energy for the cartridge 14). Other examples include other values or ranges of values. For example, in some examples the plasma treatment reduces the contact angle by at least 20 degrees, or at least 30 degrees, or at least 40 degrees.

Overall, it has been found that an increased surface energy on the surface of the cartridge 14 creates a more hydrophilic surface, which facilitates flow and attraction of blood in the wells 30, and reduces the formation of air bubbles within the wells 30. Maintaining increased surface energy throughout the life of the cartridge 14 may increase overall testing accuracy.

With continued reference to FIGS. 5 and 6, in some examples the ferromagnetic elements 38 themselves are partially or entirely coated with a hydrophilic material, to inhibit the formation of air bubbles in the wells 30. In some examples the ferromagnetic elements 38 are coated with a hydrophilic spray (e.g., a Lotus™ spray), thus creating hydrophilic surfaces on the ferromagnetic elements 38. It has been found that coating the ferromagnetic elements 38 lowers the contact angle on the surface of the ferromagnetic elements 38 anywhere between, for example 20 to 40 degrees, and maintains that lowered contact angle for example up to a year. Other examples include other values and ranges of values. For example, in some examples the coating reduces the contact angle by at least 20 degrees, or at least 30 degrees, or at least 40 degrees.

Accurately measuring the clotting time of the blood sample (i.e., the time for the blood to change in viscosity and coagulate) within the cartridge 14 may be highly dependent on the reactivity of the materials the blood comes in contact with. Therefore, in some examples, the ferromagnetic elements 38 are partially or entirely coated (e.g., plated) with a substance that has little or no reactivity with the blood inside the cartridge 14. It has been found that gold, for example, has almost no reactivity with blood samples. Therefore, in some examples, the ferromagnetic elements 38 are partially or entirely coated with gold (e.g., in addition to or in place of being spray coated with a hydrophilic spray), or other metallic material. In some examples, the ferromagnetic elements 38 are partially or entirely coated with nickel-titanium (NiTi), zinc, and/or tin.

Figure 7:
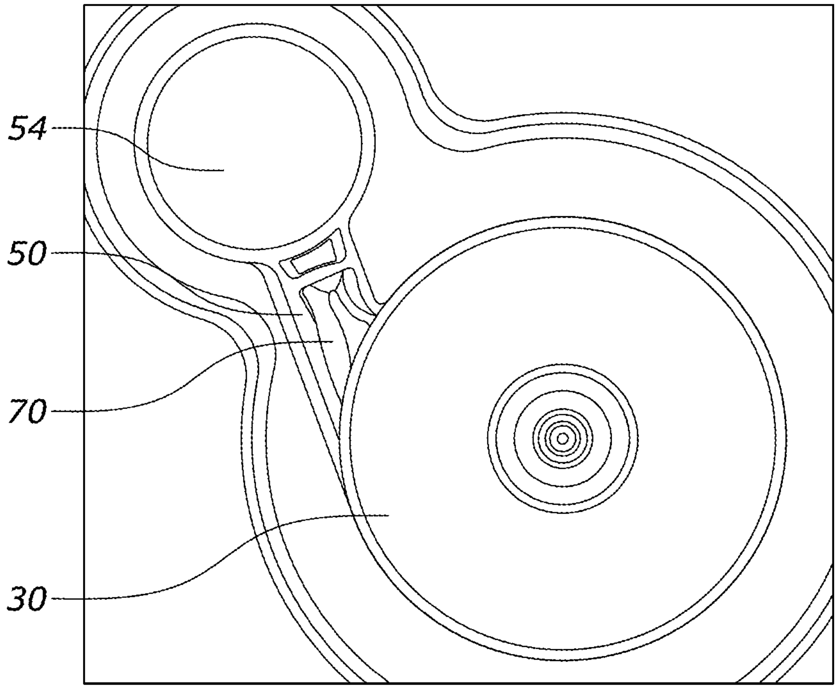
FIG. 7 is a partial, top plan view of the cartridge, illustrating an outlet conduct that extends between one of the wells and a vent, the outlet conduit coated in a hydrophobic material.
Figure 8:
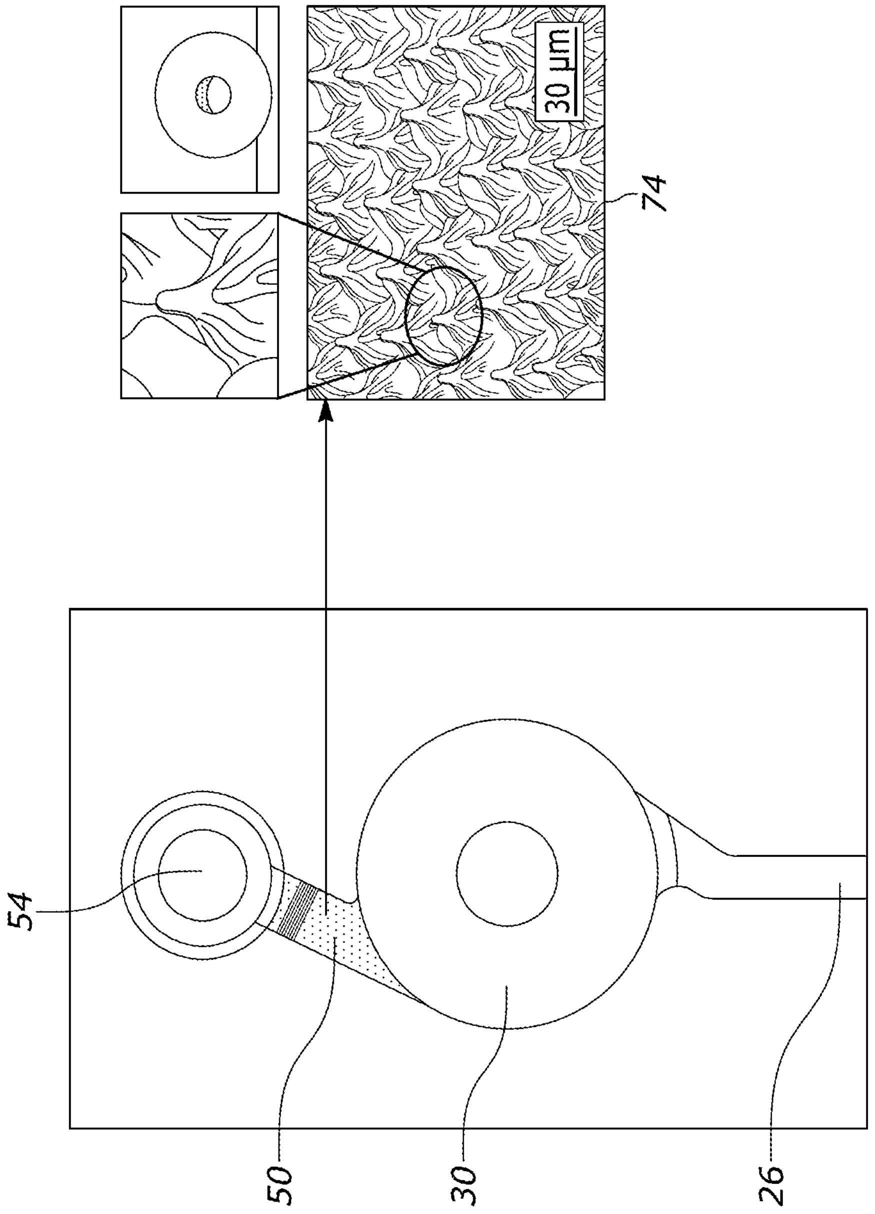
FIG. 8 is a partial, top plan view of the cartridge, illustrating an outlet conduit that extends between one of the wells and a vent, the outlet conduit having a microtextured, hydrophobic surface.

With reference to FIGS. 7 and 8, and as described above, the cartridge 14 includes outlet conduits 50 that extend from the wells 30 to the air vent apertures 46. The outlet conduits 50 are used, for example, to facilitate movement of any air to the vent apertures 46, so that the air may be removed from the cartridge 14 through the vent apertures 46. In the illustrated example, each of the outlet conduits 50 includes a hydrophobic surface, to stall the flow of blood until the air has evacuated from through the vent apertures 46. The hydrophobic surface may be created in different manners, for example by coating a material onto the existing surface of the cartridge 14 at the outlet conduit 50, or forming the outlet conduit 50 itself to have a hydrophobic surface during an initial manufacturing step, or working the material of the cartridge 14 after manufacturing the cartridge 14.

With reference to FIG. 7, in some examples a siloxane material 70 (e.g., a small amount of siloxane adhesive) is applied and coated onto the surface of the cartridge 14 at the outlet conduits 50. In the illustrated example, the siloxane material 70 is located only along a portion of the outlet conduit 50, whereas the rest of the outlet conduit 50 may for example have a hydrophilic surface. The cured surface formed by the siloxane material 70, however, is hydrophobic. As illustrated in FIG. 7, different types of cartridges 14 (e.g., those with round, circular wells 30 and corresponding ferromagnetic elements 38, and those with elliptical wells 30 and corresponding ferromagnetic elements 38) were tested using this approach. The ferromagnetic elements 38 in each test were coated with a hydrophilic spray. As seen in the chart in FIG. 7, the formation of air bubbles in the wells 30 was significantly reduced, particularly in round wells 30.

With reference to FIG. 8, in some examples the hydrophobic surface at the outlet conduit 50 is a microtextured surface 74. Using a microtextured surface 74 is a more permanent solution, and in some examples will not degrade over the shelf-life of the cartridge 14. In the illustrated example, the microtextured surface 74 includes small (e.g., microscopic) peaks and valleys, and an overall roughness that forms the hydrophobic surface, in the illustrated example, the microtextured surface 74 is located only along a portion of the outlet conduit 50. The rest of the outlet conduit 50 includes, for example, a hydrophilic surface. In some examples, the microtextured surface 74 is formed during an initial manufacturing step (e.g., molded in place during formation of the main body 18 of the cartridge 14). Alternatively, in other examples the microtextured surface 74 is formed after an initial manufacturing step, by a working process (e.g., machining, etc.) performed on the main body 18 of the cartridge 14.

Overall, the creation of the hydrophilic and/or hydrophobic surfaces on the cartridge 14 (e.g., within the wells 30 and/or the outlet conduits 50 and/or on the ferromagnetic elements 38), and/or the use of coating (e.g., plating) of the ferromagnetic elements 38 as described above, may inhibit the formation of air bubbles in the cartridge 14, and in general facilitate better (e.g., more accurate, repeatable) testing results.

Figure 9:
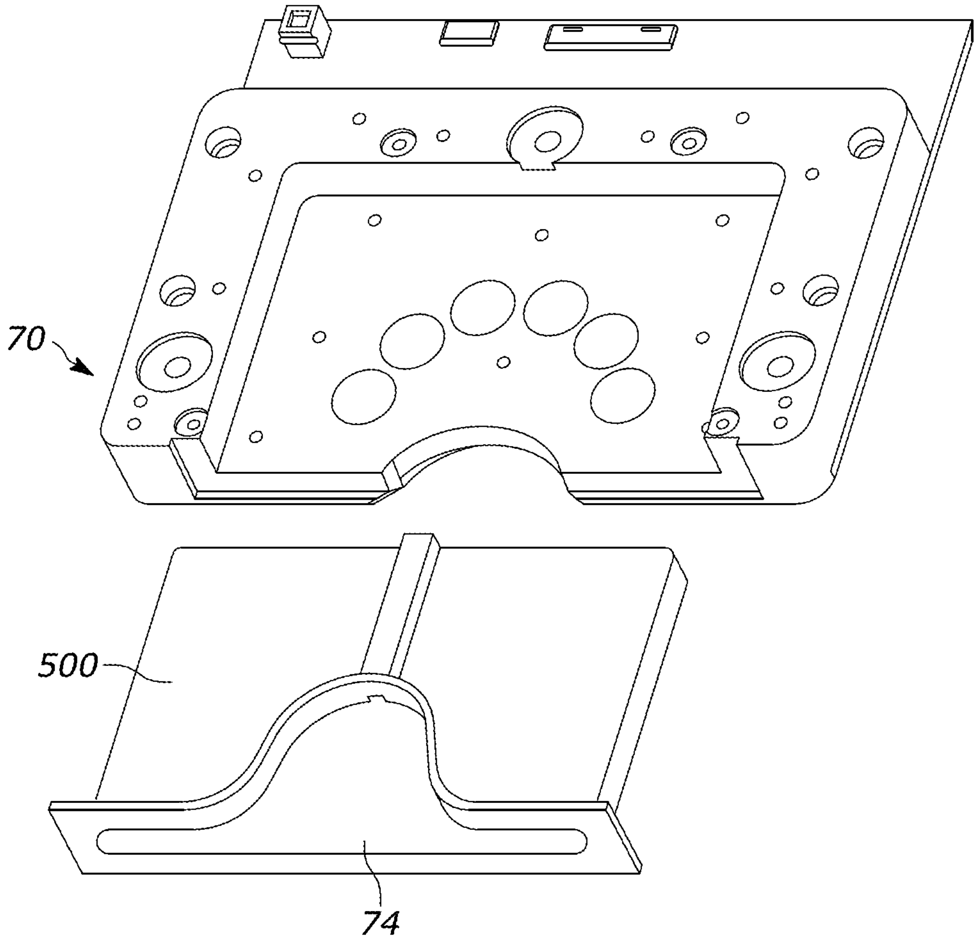
FIGS. 9 and 10 are perspective views of a removable slot housing for the cartridge.
Figure 10:
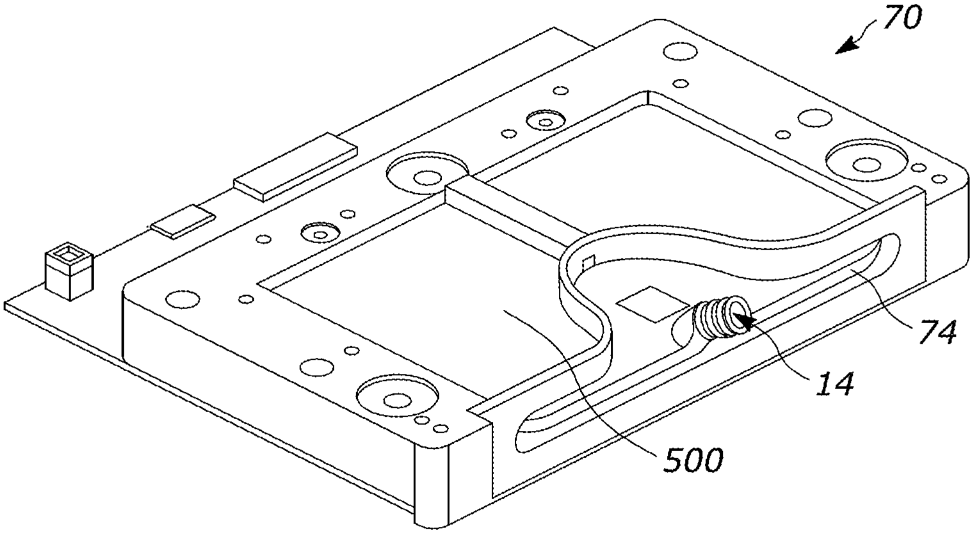

With reference to FIGS. 9 and 10, in some examples the device 10 includes a removable and washable slot housing 500 that forms the cartridge slot 74. The removable slot housing 500 facilitates easy cleaning of the cartridge slot 74, which may be beneficial, particularly if the device 10 is being used in an operating room with blood. In some examples, the slot housing 500 is an injection-molded alumina sleeve. The slot housing 500 may take the place of position and fill sensor caps. In the illustrated example, the alumina slot housing 500 permits conduction of heat, but does not affect any position and fill sensor performance as a metal component might. Alumina also tolerates harsh cleaners without degrading or corroding. The slot housing 500 may be reused several times, or can easily be replaced or interchanged. In yet other examples the slot housing 500 is a disposable plastic liner. The disposable plastic liner reduces the need for cleaning, and protects against spills or leaks.

Figure 11:
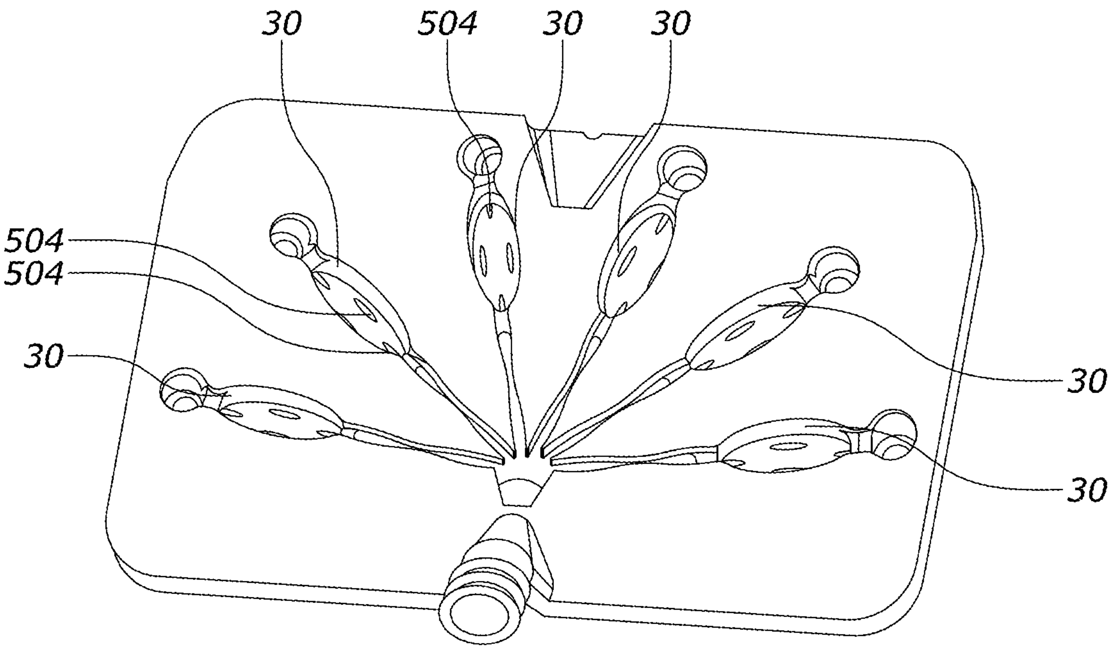
FIG. 11 is a perspective view of elliptical-shaped wells in the cartridge, and standoffs at the bottoms of the wells.
Figure 12:
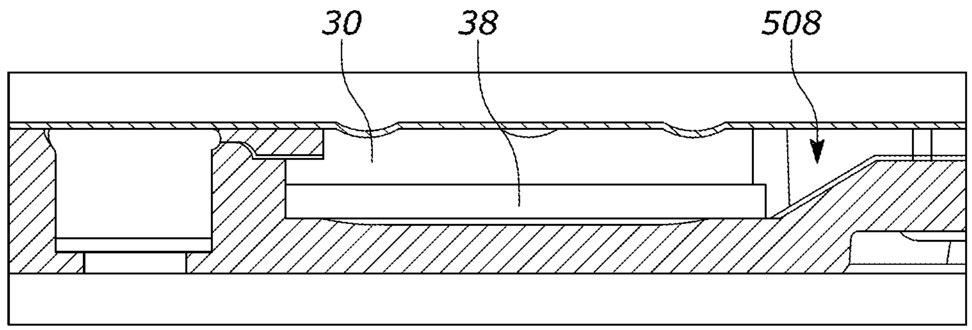
FIG. 12 is a perspective view of a ramped inlet for one of the wells.

With reference to FIGS. 11 and 12, and as described above, in some examples the wells 30 have an oval (e.g., elliptical) shape. It has been discovered that elliptical-shaped wells 30 reduce the occurrence rate of large air entrapment in the wells 30 by providing a smoother transition and more laminar flow. With reference to FIG. 11, in some examples the wells 30 additionally, or alternatively, include standoffs 504 along the bottoms of the wells 30. The standoffs 504 allow fluid to flow under the ferromagnetic elements 38 and allow air to evacuate. With reference to FIG. 12, in some examples the wells 30 additionally, or alternatively, include ramped inlets 508. The ramped inlets 508 provide a smoother transition into the wells 30, provide a more laminar flow, reduce the likelihood of air being trapped at sharp corners, and help to encourage flow under the ferromagnetic elements 38.

Figure 13:
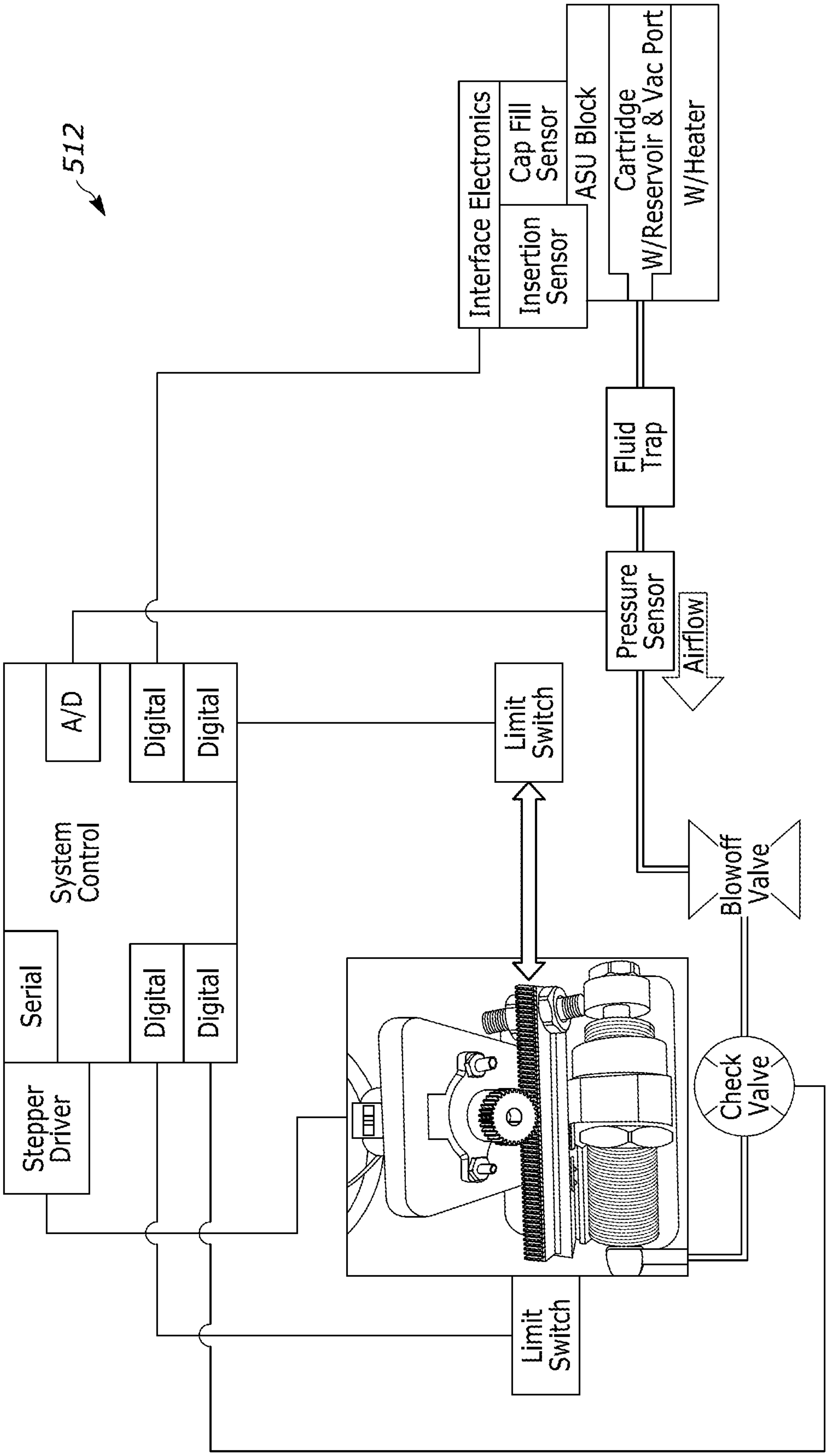
FIG. 13 is a schematic view of an automated vacuum fill system.

With reference to FIG. 13, in some examples the device 10 includes an automated vacuum fill system 512 (e.g., having system control, stepper driver, limit switches, pressure sensors, valves, interfaces, and/or other components) that allows the cartridge 14 and the wells 30 to be filled automatically (e.g., hands-free) with the sample fluid. The system 512 may reduce the chance of air entrapment, increase instrument accuracy and cycle time, and/or permit the user to focus more time on the patient. In the illustrated example, the system 512 includes a syringe pump that creates negative pressure in the cartridge wells 30. That pressure is then equilibrated with the fluid. The user is not required to manually control the fill speed or dispensed volume. In some examples, the system 512 provides higher cartridge reliability (e.g., inhibiting cartridge burst), and/or doubles as a fill sensor.

Figure 14:
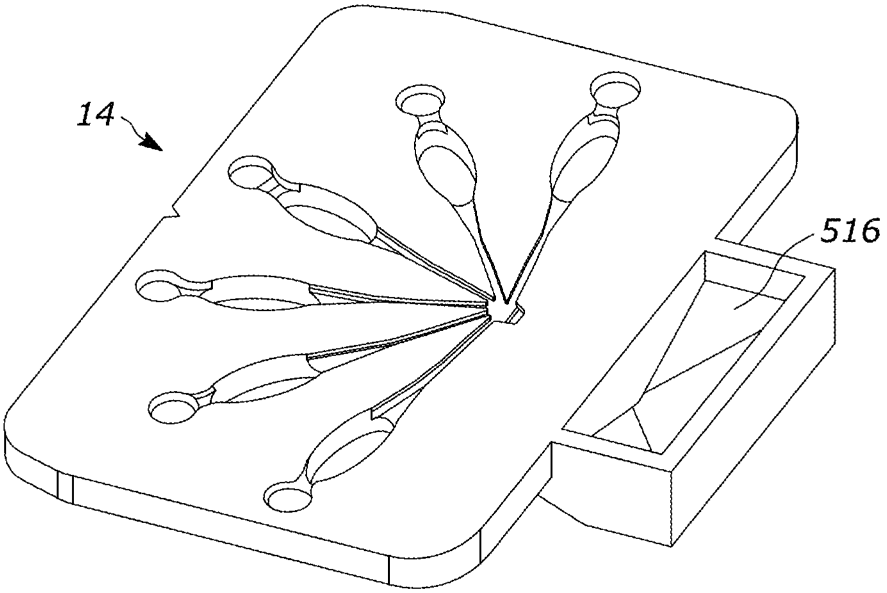
FIG. 14 is a perspective view of an external fluid reservoir.

With reference to FIG. 14, in some examples the device 10 includes an external fluid reservoir 516 at a front of the cartridge 14. The user may dispense fluid into this reservoir 516 in preparation for an automatic fill of the cartridge 14. This may reduce interaction time (e.g., the user may simply fill and then walk away). The user is not required to control the dispensed volume, and excess fluid may be disposed.

Figure 15:
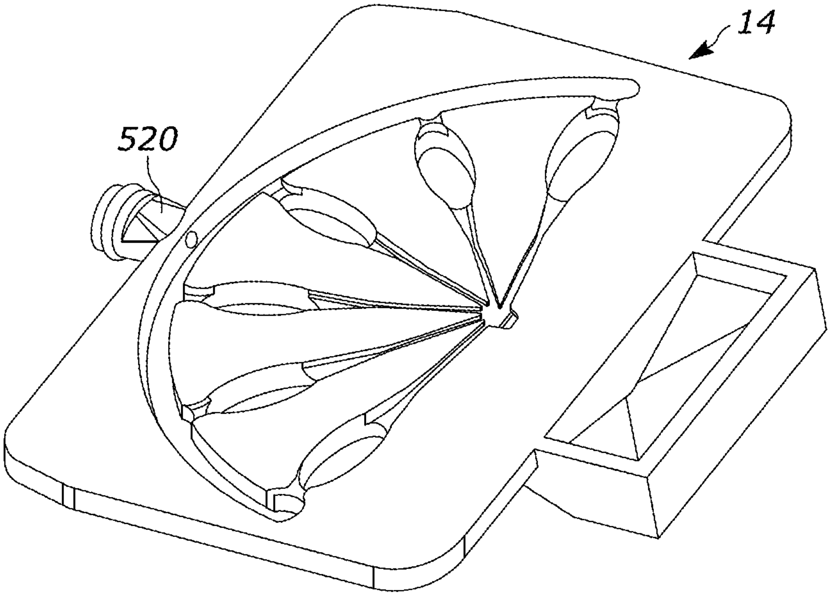
FIG. 15 is a perspective view of a vacuum fill cartridge port.

With reference to FIG. 15, in some examples the device 10 includes a vacuum fill cartridge port 520 that hermetically seals with a syringe pump at a single point. The port 520 may leverage cartridge alignment features for port alignment. In some examples, fluid traps ensure that the pump remains uncontaminated. Additionally, sealing (e.g., O-ring) may be provided on the cartridge 14 to increase reliability.

Although various aspects and examples have been described in detail with reference to certain examples illustrated in the drawings, variations and modifications exist within the scope and spirit of one or more independent aspects described and illustrated.

What is claimed is:

1. A device for measuring viscosity of a fluid, the device comprising:

a cartridge having a cartridge main body including an injection port configured to introduce fluid into the cartridge;

a plurality of inlet conduits coupled to and extending away from the injection port; and a plurality of wells, wherein the inlet conduits extend from the injection port to the wells, and are configured to deliver the fluid from the injection port to the wells;

a plurality of ferromagnetic elements configured to sit within the wells, wherein each of the ferromagnetic elements includes a metallic plating;

wherein the cartridge main body includes a hydrophilic surface to inhibit the formation of air bubbles within the wells.

2. The device of claim 1, wherein the hydrophilic surface is a coating within the wells.

3. The device of claim 1, wherein the hydrophilic surface is a plasma-treated surface of the cartridge.

4. The device of claim 1, wherein the hydrophilic surface is within at least one of the inlet conduits or the wells.

5. The device of claim 1, wherein each of the ferromagnetic elements is coated with a hydrophilic spray.

6. The device of claim 1, wherein the metallic plating is a gold plating.

7. The device of claim 1, wherein the metallic plating is a zinc plating.

8. The device of claim 1, wherein each of the ferromagnetic elements is also coated with a hydrophilic spray.

9. The device of claim 1, wherein each of the ferromagnetic elements is a washer-like element having a circular shape and central aperture.

10. The device of claim 1, wherein the cartridge includes a plurality of outlet conduits and a plurality of vents, wherein the outlet conduits extend from the wells to the vents, wherein each of the outlet conduits includes a hydrophobic surface.

11. A device for measuring a viscosity of a fluid, the device comprising:

a cartridge having an injection port configured to introduce fluid into the cartridge;

a plurality of inlet conduits coupled to and extending away from the injection port;

a plurality of wells, wherein the inlet conduits extend from the injection port to the wells, and are configured to deliver the fluid from the injection port to the wells;

a plurality of outlet conduits; and a plurality of vents;

wherein the outlet conduits extend from the wells to the vents, and wherein each of the outlet conduits includes a hydrophobic surface, wherein the hydrophobic surface is a hydrophobic coating, and wherein the hydrophobic coating is a siloxane coating.

12. The device of claim 11, wherein the hydrophobic coating is a cured siloxane adhesive.

13. The device of claim 11, wherein each of the outlet conduits also includes a hydrophilic surface.

14. A method of manufacturing a device for measuring viscosity of a fluid, the method comprising:

providing a cartridge having an injection port configured to introduce fluid into the cartridge, a plurality of inlet conduits coupled to and extending away from the injection port, a plurality of wells, wherein the inlet conduits extend from the injection port to the wells, and are configured to deliver the fluid from the injection port to the wells, a plurality of outlet conduits, and a plurality of vents, wherein the outlet conduits extend from the wells to the vents;

applying a hydrophilic coating to each of a plurality of ferromagnetic elements and inserting the ferromagnetic elements into the wells; and forming a hydrophobic surface on each of the outlet conduits.

15. The method of claim 14, wherein the hydrophilic coating is a gold plating, and wherein the hydrophobic surface is a microtextured surface.

* * * * *